United States Patent
Gronberg et al.

(10) Patent No.: US 10,857,150 B2
(45) Date of Patent: Dec. 8, 2020

(54) USE OF SANGLIFEHRIN MACROCYCLIC ANALOGUES AS ANTICANCER COMPOUNDS

(71) Applicant: NEUROVIVE PHARMACEUTICAL AB, Lund (SE)

(72) Inventors: Alvar Gronberg, Knivsta (SE); Magnus Joakim Hansson, Landskrona (SE); Matthew Alan Gregory, Bourn (GB); Steven James Moss, Balsham (GB)

(73) Assignee: ABLIVA AB, Lund (SE)

( * ) Notice: Subject to any disclaimer, the term of this patent is extended or adjusted under 35 U.S.C. 154(b) by 0 days.

(21) Appl. No.: 16/349,757

(22) PCT Filed: Nov. 17, 2017

(86) PCT No.: PCT/EP2017/079549
§ 371 (c)(1),
(2) Date: May 14, 2019

(87) PCT Pub. No.: WO2018/091634
PCT Pub. Date: May 24, 2018

(65) Prior Publication Data
US 2019/0328734 A1  Oct. 31, 2019

(30) Foreign Application Priority Data

Nov. 18, 2016  (DK) .................. 2016 70920
Jan. 30, 2017   (DK) .................. 2017 70054

(51) Int. Cl.
| | |
|---|---|
| *C07D 498/08* | (2006.01) |
| *A61K 31/50* | (2006.01) |
| *A61K 31/44* | (2006.01) |
| *A61K 31/704* | (2006.01) |
| *A61K 39/395* | (2006.01) |
| *C07D 237/04* | (2006.01) |

(52) U.S. Cl.
CPC .............. *A61K 31/50* (2013.01); *A61K 31/44* (2013.01); *A61K 31/704* (2013.01); *A61K 39/3955* (2013.01); *C07D 237/04* (2013.01); *C07D 498/08* (2013.01)

(58) Field of Classification Search
CPC ............................. C07D 491/06; C07D 498/08
See application file for complete search history.

(56) References Cited

U.S. PATENT DOCUMENTS

| | | | |
|---|---|---|---|
| 4,475,916 A | 10/1984 | Himmelstein | |
| 2014/0234414 A1* | 8/2014 | Gregory | A61K 9/4891 424/463 |

FOREIGN PATENT DOCUMENTS

WO    2012/131377 A1    10/2012

OTHER PUBLICATIONS

Hopkins, et al., "SCY-635, a novel nonimmunosuppressive analog of cyclosporine that exhibits potent inhibition of hepatitis C virus RNA replication in vitro" Antimicrob. Agents Chemother. (2010) 54(2):660-72.
Inoue, et al., "Combined interferon alpha2b and cyclosporin A in the treatment of chronic hepatitis C: controlled trial" J. Gastroenterol. (2003) 38(6):567-72.
Hartel, et al., "Immunosuppressive activity of the immunophilin-binding drug Sanglifehrin A in human whole blood: potent inhibition of interleukin-6 produced by lymphocytes and monocytes" Scand. J. Immunol. (2006) 63(1):26-34.
Moss, et al., "Sangamides, a new class of cyclophilin-inhibiting host-targeted antivirals for treatment of HCV infection" Med. Chem. Commun. (2012) 3(8):938-943.
Han, et al., "Cyclosporin A and sanglifehrin A enhance chemotherapeutic effect of cisplatin in C6 glioma cells" Oncol. Rep. (2010) 23(4):1053-62.
Hansson, et al., "Bioengineering and semisynthesis of an optimized cyclophilin inhibitor for treatment of chronic viral infection" Chem. Biol. (2015) 22(2):285-92.

* cited by examiner

*Primary Examiner* — Emily A Bernhardt
(74) *Attorney, Agent, or Firm* — Robert C. Netter, Jr.; Dann, Dorfman, Herrell & Skillman

(57) ABSTRACT

The present invention relates to sanglifehrin macrocyclic analogues according to Formula (I),

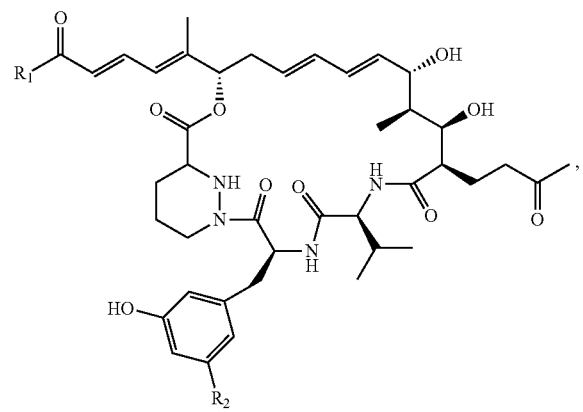

particularly for use in treatment of cancer, especially liver cancer.

2 Claims, 7 Drawing Sheets

USE OF SANGLIFEHRIN MACROCYCLIC ANALOGUES AS ANTICANCER COMPOUNDS

This application is a § 371 application of PCT/EP2017/079549, filed Nov. 17, 2017, which in turn claims priority to DK Application PA 2016 70920, filed Nov. 18, 2016, and DK Application PA 2017 70054, filed Jan. 30, 2017. The entire disclosure of each of the foregoing applications is incorporated by reference herein.

FIELD OF THE INVENTION

The present invention relates to the use of sanglifehrin macrocyclic analogues for use in the treatment of cancer or B-cell malignancy. The invention also relates to a combination of a sanglifehrin macrocyclic analogue with i) a tyrosine kinase inhibitor, ii) an inhibitor of other kinases, iii) an anti-receptor antibody, iv) a genotoxic agent, v) an inhibitor affecting DNA synthesis, DNA structure and/or topoisomerase, vi) an immune checkpoint inhibitor, or vii) a hormone, or the sanglifehrin macrocyclic analogues may be used in combination with radiotherapy or surgery. The present invention also relates to novel sanglifehrin macrocyclic analogues.

BACKGROUND OF THE INVENTION

Cyclophilin Inhibitors Cyclophilins (CyP) are a family of cellular proteins that display peptidyl-prolyl cis-trans isomerase activity facilitating protein conformation changes and folding. CyPs are involved in cellular processes such as transcriptional regulation, immune response, protein secretion, and mitochondrial function.

Cyclosporine A (Inoue, et al. (2007). Hepatology 45(4): 921-8) ("CsA") and its closely structurally related non-immunosuppressive clinical analogues DEBIO-025 (Paeshuyse, et al. (2006). Hepatology 43(4): 761-70), NIM811 (Mathy et al. 2008 Antimicrob Agents Chemother 52(9): 3267-75) and SCY-635 (Hopkins et al., 2009 J Gastroenterol 38(6): 567-72) (see FIG. 1) are known to bind to cyclophilins, and as cyclophilin inhibitors have shown in vitro and clinical efficacy in the treatment of HCV infection (Crabbe et al., 2009 Expert Opin Investig Drugs 18(2): 211-20).

The anti-HCV effect of cyclosporine analogues is independent of the immunosuppressive property, which is dependent on calcineurin, the same target as FK506 (Liu et al., Cell 1991 66:807-815).

Sanglifehrins

Sanglifehrin A (SfA) and its natural congeners belong to a class of mixed non-ribosomal peptide/polyketides, produced by *Streptomyces* sp. A92-308110 (also known as DSM 9954) (see WO 97/02285), which were originally discovered on the basis of their high affinity to cyclophilin A (CyPA) (see FIG. 2 for example structures). SfA is the most abundant component in fermentation broths and exhibits approximately 20-fold higher affinity for CyPA compared to CsA. Sanglifehrins have also been shown to exhibit a lower immunosuppressive activity than CsA when tested in vitro in assays such as mixed lymphocyte reactions (Sanglier et al., 1999; Fehr et al., 1999). SfA binds with high affinity to the CsA binding site of CyPA (Kallen et al., 2005 J Biol Chem 280(23): 21965-71).

The 'immunosuppressive' mechanism of action of SfA is different to that of other known immunophilin-binding immunosuppressive drugs such as CsA, FK506 and rapamycin. SfA does not inhibit the phosphatase activity of calcineurin, the target of CsA (Zenke et al. 2001 J Immunol 166(12): 7165-71), instead its 'immunosuppressive' activity has been attributed to the inhibition of interleukin-6 (Hartel et al., 2005 Scand J Immunol 63(1): 26-34), interleukin-12 (Steinschulte et al., 2003 J Immunol 171(2): 542-6) and inhibition of interleukin-2-dependent T cell proliferation (Zhang & Liu, 2001 J Immunol 166(9): 5611-8). However, the molecular target and mechanism through which SfA exerts its 'immunosuppressive' effect is hitherto unknown.

The molecular structure of SfA is complex and its interaction with CyPA has been proposed to be mediated largely by the macrocyclic portion of the molecule. In fact, a macrocyclic compound (hydroxymacrocycle) derived from oxidative cleavage of SfA has shown strong affinity for CyPA (Sedrani et al., 2003). X-ray crystal structure data has shown that the hydroxymacrocycle binds to the same active site of CyPA as CsA. Analogues based on the macrocycle moiety of SfA have also been shown to be devoid of 'immunosuppressive' properties (Sedrani et al., 2003 J Am Chem Soc 125(13): 3849-59). A number of macrocyclic analogues with potent Cyclophilin inhibition have been published (e.g. WO2011/098809, WO2011/144924, WO2011/098808, WO2012/085553, WO2011/098805, WO2012/131371, WO2012/131377, Hansson et al., 2015 Chem Biol. 2015 Feb. 19; 22(2): 285-292), in particular, compounds 9 and NV556, 10 (see FIG. 2). The first of these, compound 9 is described in WO2011/098805, and was shown to have limited effect on three cancer cell lines Huh7, HepG2 and OEM. In fact, it was stated as being "less cytotoxic than sanglifehrin A in three out of the four cell lines tested".

Cyclophilin Inhibitors and Cancer

Cyclophilins are one of the most important classes of proteins, because they guarantee the correct functioning of the entire proteome, by folding client peptides in the proper way. For this reason, cancer cells overexpress the genes encoding for cyclophilins, so to have a very efficient protein folding machinery, able to sustain their dramatic proliferation rate (Lavin et al., Curr Mol Pharmacol. 2015; 9(2):148-64). Targeting cyclophilins has at least two advantages: it tackles a plethora of cellular functions in cancer cells and has minimal toxicity on normal cells.

Since most anticancer drugs acts by directly targeting proteins or causing cell damage requiring their intervention, cancer cells cope with these mechanisms of action by synthesizing more of these proteins, relying upon cyclophilins to fold them (Obacz et al., Sci Signal. 2017 Mar. 14; 10(470), McConkey, Biochem Biophys Res Commun. 2017 Jan. 15; 482(3):450-453, Vahid et al, Recent Pat Anticancer Drug Discov. 2017; 12(1):35-47.

It has long been known that cyclophilins are overexpressed in a number of cancers and that cyclophilin A is a key determinant for malignant transformation and metastasis (Nigro et al., 2013, Cell Death and Disease 4, e888; doi:10.1038/cddis.2013.410). It has also been noted that CsA and sanglifehrin A (SfA), increase the chemotherapeutic effect of cisplatin in glioblastoma multiforme (Han et al., Oncol Rep 2010; 23: 1053-1062). CyPA overexpression has also been shown to decrease cisplatin-induced cell death, whereas CyPA knockdown lowers cell survival rates (Choi et al., Cancer Res 2007; 67: 3654-3662). In vivo studies have also been conducted using cyclophilin knockdowns, leading to significant effects (Howard et al., Cancer Res 2005; 65: 8853-8860). Overexpression of CyPA has also been seen to generate faster growing xenografts in SCID mice compared with cells transfected with the empty vector. Intra-tumour injection of Pgenesil-2-CypA-shRNA also decreased tumour development in nude mice (Li et al., Mol Cell Proteomics 2008; 7: 1810-1823).

Genetic deletion or pharmacological suppression of cyclophilin D (CyPD) efficiently prevents Ras-dependent tumor formation and mammary tumor growth in xenograft and K-Ras lung cancer mouse models (Bigi et al., Oncogene. 2016 Sep. 29; 35(39):5132-43). CyPD has been shown to interact with p53, which acts as a tumor suppressor protein. TP53 exon-6 truncating mutations occur at higher than expected frequencies and produce proteins that lack canonical p53 tumor suppressor activities. These mutants can localize to the mitochondria where they promote tumor phenotypes by binding and activating the mitochondria inner pore permeability regulator, CyPD (Shirole et al., eLife. 2016; 5: e17929).

However, despite this prevalence of literature suggesting the relevance of cyclophilins in cancer, little or no evidence has suggested that any of the potent and specific cyclophilin inhibitors leads to a potent in vivo effect on cancer in a clinical setting.

The inventors have surprisingly discovered that certain sanglifehrin macrocyclic analogues lead to a much more potent inhibition of cancer cell growth than other cyclophilin inhibitors, possibly through an entirely different mechanism to other cyclophilin inhibitors, especially those based on cyclosporine A.

Therefore, the present invention provides for the medical use of sanglifehrin macrocyclic analogues, these sanglifehrin macrocyclic analogues having more potent inhibition of cancer cell growth. These compounds are useful in medicine, in particular for the treatment of cancer and/or B-cell malignancies. The present invention particularly provides for the use of sanglifehrin macrocyclic esters in the treatment of cancer and/or B-cell malignancies.

The present invention provides the novel and surprising use of sanglifehrin macrocyclic analogues in medicine, in particular the use of sanglifehrin macrocyclic esters, particularly in the treatment of cancer or B-cell malignancies. In particular, the present invention provides for the use of sanglifehrin macrocyclic analogues in the treatment of cancer and B-cell malignancies. In a further preferred embodiment, the present invention provides for the use of sanglifehrin macrocyclic analogues in the treatment of liver cancer, in particular, hepatocellular carcinoma (HCC). In a specific aspect of the present invention, the sanglifehrin analogue is sanglifehrin macrocyclic esters.

SUMMARY OF THE INVENTION

The present invention relates to the medical use of sanglifehrin macrocyclic analogues, in particular, sanglifehrin macrocyclic esters, particularly in the treatment of cancer and/or B-cell malignancies. In particular, this invention relates to the use of sanglifehrin macrocyclic analogues for the treatment of cancer and/or B-cell malignancies. In an embodiment the present invention relates to the use of sanglifehrin macrocyclic esters in the treatment of cancer and/or B-cell malignancies. The present invention also specifically provides for the use of sanglifehrin macrocyclic analogues in the treatment of liver cancer, and for the use of sanglifehrin macrocyclic analogues or sanglifehrin macrocyclic esters in the treatment of HCC. The present invention also relates to a combination of a sanglifehrin macrocyclic analogue with one or more of a drug substance belonging to the classes of drug substances mentioned herein.

Definitions

The articles "a" and "an" are used herein to refer to one or to more than one (i.e. at least one) of the grammatical objects of the article. By way of example "an analogue" means one analogue or more than one analogue.

As used herein, the term "cancer" refers to a malignant or benign growth of cells in skin or in body organs, for example but without limitation, breast, prostate, lung, kidney, pancreas, brain, stomach or bowel. A cancer tends to infiltrate into adjacent tissue and spread (metastasis) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer and ovarian cancer.

As used herein the term "liver cancer" refers to a malignant or benign growth of cells in the liver, it includes primary and secondary (metastatic) tumours. Primary liver cancers include, without limitation, hepatocellular carcinoma (liver cell carcinoma), intrahepatic cholangiocarcinoma (peripheral bile duct carcinoma), bile duct cystadenocarcinoma, combined hepatocellular and cholangiocarcinoma, hepatoblastoma and undifferentiated carcinoma. The term "liver tumours" is also used to describe the above set of disorders and these terms are used interchangeably herein.

As used herein the term "B-cell malignancies" includes a group of disorders that include chronic lymphocytic leukaemia (CLL), multiple myeloma, and non-Hodgkin's lymphoma (NHL). They are neoplastic diseases of the blood and blood forming organs. They cause bone marrow and immune system dysfunction, which renders the host highly susceptible to infection and bleeding.

As used herein the term "cancer or B-cell malignancy resistant to one or more existing anticancer agent(s)" refers to cancers or B-cell malignancies for which at least one typically used therapy is ineffective. These cancers are characterised by being able to survive after the administration of at least one neoplastic agent where the normal cell counterpart (i.e., a growth regulated cell of the same origin) would either show signs of cell toxicity, cell death or cell quiescence (i.e., would not divide). In particular, this includes multiple drug resistance (MDR) cancers or B-cell malignancies, particular examples are cancers and B-cell malignancies which express high levels of P-gp. The identification of such resistant cancers or B-cell malignancies is within the ability and usual activities of a physician or other similarly skilled person.

As used herein the term "sanglifehrin macrocyclic analogues" refers to a compound according to formula (I) below, or a pharmaceutically acceptable salt thereof.

Formula I

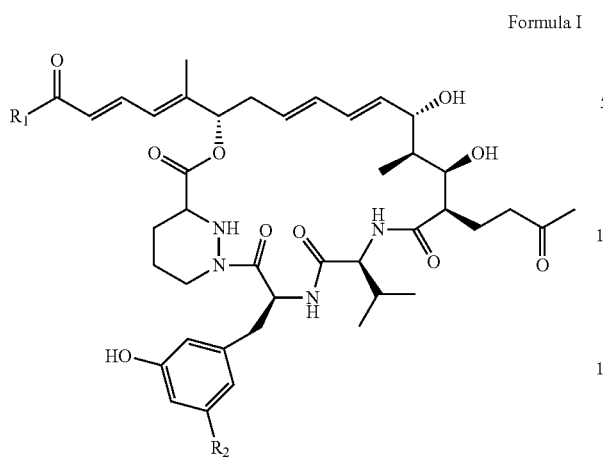

Formula II

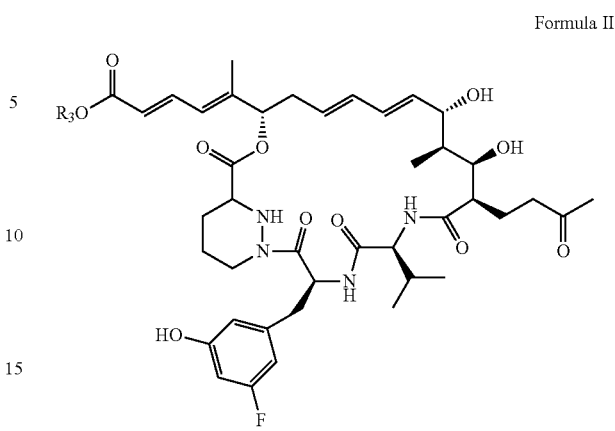

wherein, R₁ represents OR₃ or NR₃R₄, R₂ represents H or F;

and wherein R₃ and R₄ independently represent hydrogen, alkyl, alkenyl, cycloalkyl, cycloalkenyl, aryl, or heteroaryl, any of which groups may optionally be substituted by monocylic aryl or monocyclic heteroaryl;

and wherein one or more carbon atoms of R₃ and R₄ not being part of an aryl or heteroaryl group are optionally replaced by a heteroatom selected from O, N and S(O)p in which p represents 0, 1 or 2 and wherein one or more carbon atoms of R₃ and R₄ are optionally replaced by carbonyl;

or R₃ and R₄ are linked such that NR₃R₄ represents a saturated or unsaturated heterocyclic ring containing the specified nitrogen atom and wherein one or more carbon atoms of said ring are optionally replaced by a further heteroatom selected from O, N and S(O)p in which p represents 0, 1 or 2 and wherein one or more carbon atoms of said ring are optionally replaced by carbonyl and which heterocyclic ring may optionally be fused to an aryl or heteroaryl ring;

and wherein one or more carbon atoms of an R₃ and R₄ group may optionally be substituted by one or more halogen atoms, or a pharmaceutically acceptable salt thereof.

These compounds are also referred to as the "compounds of the invention" and these terms are used interchangeably in the present application. The novel sanglifehrin macrocyclic analogues are also part of the present invention.

As used herein the term "sanglifehrin macrocyclic esters" refers to a compound according to formula (I), wherein R₁=OR₃ and wherein R₂=F; or a pharmaceutically acceptable salt thereof. In another format, this can be described as formula II below:

In the present application, the term "sanglifehrin macrocyclic analogues" includes sanglifehrin macrocyclic esters.

The pharmaceutically acceptable salts of sanglifehrin macrocyclic analogues include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. References hereinafter to a compound according to the invention include both sanglifehrin macrocyclic analogues and sanglifehrin macrocyclic esters and their pharmaceutically acceptable salts.

As used herein the term "alkyl" refers to any straight or branched chain composed of only spa carbon atoms, fully saturated with hydrogen atoms such as e.g. —$C_nH_{2n+1}$ for straight chain alkyls, wherein n can be in the range of 1 and 10 such as e.g. methyl, ethyl, propyl, isopropyl, n-butyl, isobutyl, sec-butyl, tert-butyl, n-pentyl, neopentyl, isopentyl, hexyl, isohexyl, heptyl, octyl, nonyl or decyl. The alkyl as used herein may be further substituted.

As used herein the term "cycloalkyl" refers to a cyclic/ring structured carbon chains having the general formula of —$C_nH_{2n+1}$ where n is between 3-10, such as e.g. cyclopropyl, cyclobutyl, cyclopentyl, cyclohexyl, cycloheptyl or cyclooctyl, bicycle[3.2.1]octyl, spiro[4,5]decyl, norpinyl, norbonyl, norcapryl, adamantly and the like. The cycloalkyl as used herein may be further substituted.

As used herein, the term "alkenyl" refers to a straight or branched chain composed of carbon and hydrogen atoms wherein at least two carbon atoms are connected by a double bond such as e.g. $C_{2-10}$ alkenyl unsaturated hydrocarbon chain having from two to ten carbon atoms and at least one double bond. $C_{2-6}$ alkenyl groups include, but are not limited to, vinyl, 1-propenyl, allyl, iso-propenyl, n-butenyl, n-pentenyl, n-hexenyl and the like. The alkenyl as used herein may be further substituted.

As used herein the term "cycloalkenyl" refers to a cyclic/ring structured carbon chains having the general formula of —$C_nH_{2n-1}$ where n is between 3-10, wherein at least two carbon atoms are connected by a double bond. The cycloalkenyl as used herein may be further substituted.

The term "$C_{1-10}$ alkoxy" in the present context designates a group —O—$C_{1-10}$ alkyl used alone or in combination, wherein $C_{1-10}$ alkyl is as defined above. Examples of linear alkoxy groups are methoxy, ethoxy, propoxy, butoxy, pentoxy and hexoxy. Examples of branched alkoxy are iso-propoxy, sec-butoxy, tert-butoxy, iso-pentoxy and iso-hexoxy. Examples of cyclic alkoxy are cyclopropyloxy, cyclobutyloxy, cyclopentyloxy and cyclohexyloxy.

The term "$C_{3-7}$ heterocycloalkyl" as used herein denotes a totally saturated heterocycle like a cyclic hydrocarbon containing one or more heteroatoms selected from nitrogen, oxygen and sulphur independently in the cycle. Examples of heterocycles include, but are not limited to, pyrrolidine (1-pyrrolidine, 2-pyrrolidine, 3-pyrrolidine, 4-pyrrolidine, 5-pyrrolidine), pyrazolidine (1-pyrazolidine, 2-pyrazolidine, 3-pyrazolidine, 4-pyrazolidine, 5-pyrazolidine), imidazolidine (1-imidazolidine, 2-imidazolidine, 3-imidazolidine, 4-imidazolidine, 5-imidazolidine), thiazolidine (2-thiazolidine, 3-thiazolidine, 4-thiazolidine, 5-thiazolidine), piperidine (1-piperidine, 2-piperidine, 3-piperidine, 4-piperidine, 5-piperidine, 6-piperidine), piperazine (1-piperazine, 2-piperazine, 3-piperazine, 4-piperazine, 5-piperazine, 6-piperazine), morpholine (2-morpholine, 3-morpholine, 4-morpholine, 5-morpholine, 6-morpholine), thiomorpholine (2-thiomorpholine, 3-thiomorpholine, 4-thiomorpholine, 5-thiomorpholine, 6-thiomorpholine), 1,2-oxathiolane (3-(1,2-oxathiolane), 4-(1,2-oxathiolane), 5-(1,2-oxathiolane)), 1,3-dioxolane (2-(1,3-dioxolane), 3-(1,3-dioxolane), 4-(1,3-dioxolane)), tetrahydropyrane (2-tetrahydropyrane, 3-tetrahydropyrane, 4-tetrahydropyrane, 5-tetrahydropyrane, 6-tetrahydropyrane), hexahydropyradizine, (1-(hexahydropyradizine), 2-(hexahydropyradizine), 3-(hexahydropyradizine), 4-(hexahydropyradizine), 5-(hexahydropyradizine), 6-(hexahydropyradizine)).

The term "$C_{1-10}$alkyl-$C_{3-10}$ cycloalkyl" as used herein refers to a cycloalkyl group as defined above attached through an alkyl group as defined above having the indicated number of carbon atoms.

The term "aryl" as used herein is intended to include carbocyclic aromatic ring systems. Aryl is also intended to include the partially hydrogenated derivatives of the carbocyclic systems enumerated below.

The term "heteroaryl" as used herein includes heterocyclic unsaturated ring systems containing one or more heteroatoms selected among nitrogen, oxygen and sulphur, such as furyl, thienyl, pyrrolyl, and is also intended to include the partially hydrogenated derivatives of the heterocyclic systems enumerated below.

The terms "aryl" and "heteroaryl" as used herein refers to an aryl, which can be optionally unsubstituted or mono-, di- or tri substituted, or a heteroaryl, which can be optionally unsubstituted or mono-, di- or tri substituted. Examples of "aryl" and "heteroaryl" include, but are not limited to, phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), phenanthrenyl, fluorenyl, pentalenyl, azulenyl, biphenylenyl, thiophenyl (1-thienyl, 2-thienyl), furyl (1-furyl, 2-furyl), furanyl, thiophenyl, isoxazolyl, isothiazolyl, 1,2,3-triazolyl, 1,2,4-triazolyl, pyranyl, pyridazinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indolyl, oxadiazolyl, isoxazolyl, quinazolinyl, fluorenyl, xanthenyl, isoindanyl, benzhydryl, acridinyl, benzisoxazolyl, purinyl, quinazolinyl, quinolizinyl, quinolinyl, isoquinolinyl, quinoxalinyl, naphthyridinyl, phteridinyl, azepinyl, diazepinyl, pyrrolyl (2-pyrrolyl), pyrazolyl (3-pyrazolyl), 5-thiophene-2-yl-2H-pyrazol-3-yl, imidazolyl (1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), isoquinolyl (1-isoquinolyl, 3-isoquinolyl, 4-isoquinolyl, 5-isoquinolyl, 6-isoquinolyl, 7-isoquinolyl, 8-isoquinolyl), quinolyl (2-quinolyl, 3-quinolyl, 4-quinolyl, 5-quinolyl, 6-quinolyl, 7-quinolyl, 8-quinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl)), indolyl (1-indolyl, 2-indolyl, 3-indolyl, 4-indolyl, 5-indolyl, 6-indolyl, 7-indolyl), indazolyl (1-indazolyl, 2-indazolyl, 3-indazolyl, 4-indazolyl, 5-indazolyl, 6-indazolyl, 7-indazolyl), benzimidazolyl, (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl).

Non-limiting examples of partially hydrogenated derivatives are 1,2,3,4-tetrahydronaphthyl, 1,4-dihydronaphthyl, pyrrolinyl, pyrazolinyl, indolinyl, oxazolidinyl, oxazolinyl, oxazepinyl and the like.

As used herein the term "acyl" refers to a carbonyl group —C(=O) R wherein the R group is any of the above defined groups. Specific examples are formyl, acetyl, propionyl, butyryl, pentanoyl, hexanoyl, heptanoyl, octanoyl, nonanoyl, decanoyl, benzoyl and the likes.

"Optionally substituted" as applied to any group means that the said group may, if desired, be substituted with one or more substituents, which may be the same or different. 'Optionally substituted alkyl' includes both 'alkyl' and 'substituted alkyl'.

Examples of suitable substituents for "substituted" and "optionally substituted" moieties include halo (fluoro, chloro, bromo or iodo), $C_{1-6}$ alkyl, $C_{3-6}$ cycloalkyl, $C_{3-6}$ cycloalkenyl hydroxy, $C_{1-6}$ alkoxy, cyano, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{1-6}$ aryl, $C_{1-6}$ arylamino, $C_{1-6}$ aroylamino, benzylamino, $C_{1-6}$ arylamido, carboxy, $C_{1-6}$ alkoxycarbonyl or ($C_{1-6}$ aryl)($C_{1-10}$ alkoxy)carbonyl, carbamoyl, mono-$C_{1-6}$ carbamoyl, di-$C_{1-6}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulfur atom may be further oxidised to make a sulfoxide or sulfone, and thus optional substituents therefore includes groups such as S(O)-alkyl and S(O)$_2$-alkyl.

Substitution may take the form of double bonds, and may include heteroatoms. Thus an alkyl group with a carbonyl (C=O) instead of a CH$_2$ can be considered a substituted alkyl group.

Substituted groups thus include for example CFH$_2$, CF$_2$H, CF$_3$, CH$_2$NH$_2$, CH$_2$OH, CH$_2$CN, CH$_2$SCH$_3$, CH$_2$OCH$_3$, OMe, OEt, Me, Et, —OCH$_2$O—, CO$_2$Me, C(O)Me, i-Pr, SCF$_3$, SO$_2$Me, NMe$_2$, CONH$_2$, CONMe$_2$ etc. In the case of aryl groups, the substitutions may be in the form of rings from adjacent carbon atoms in the aryl ring, for example cyclic acetals such as O—CH$_2$—O.

DESCRIPTION OF THE INVENTION

The present invention relates to the use of sanglifehrin macrocyclic analogues in medicine, in particular in the treatment of cancer and/or B-cell malignancies. In an embodiment, the present invention provides for the use of sanglifehrin macrocyclic esters, or a pharmaceutically acceptable salt thereof, in the treatment of cancer or B-cell malignancies.

The present invention also provides for the use of a sanglifehrin analogue, i.e. a sanglifehrin analogue with increased cytostatic activity compared to other related sanglifehrin analogues, or a pharmaceutically acceptable salt thereof, in the treatment of medical conditions where inhibition of cellular growth is important. The present invention also provides for the use of sanglifehrin macrocyclic esters, or a pharmaceutically acceptable salt thereof, in the treatment of liver cancer. Preferably, the present invention provides a method of treatment of cancer or B-cell malignancies which comprises administering to a patient an effective amount of a sanglifehrin analogue. In an embodiment the present invention provides a method of treatment of liver cancers which comprises administering to a patient an effective amount of a sanglifehrin analogue. In a specific aspect the sanglifehrin analogue is sanglifehrin macrocyclic esters.

As seen from the examples herein, a synergistic effect may be obtained by administering a sanglifehrin analogue together with another drug substance. In examples 4 and 8 a synergistic effect is demonstrated between a sanglifehrin analogue and doxorubicin (i.e. an example of a genotoxic agent) and between a sanglifehrin analogue and sorafenib (i.e. an example of a tyrosine kinase inhibitor. It is contemplated that synergistic effects also are obtained with other drug substances within the therapeutic group (see below) as well as a synergistic effect is seen between sanglifehrin analogues and other drug substances belonging to relevant therapeutic groups.

Thus, the present invention also relates to a combination of a sanglifehrin analogue and one or more of the drug substances mentioned in the following, as well as to the use of such combinations and to pharmaceutical compositions or kits containing such combinations. Moreover, a sanglifehrin analogue may be co-administered with another therapeutic agent for the treatment of cancer or B-cell malignancies. The preferred drug substances include, but are not limited to, I) Tyrosine kinase inhibitors like Sorafenib, regorafenib, acalabrutinib, afatinib, alectinib, axitinib, bosutinib, brigatinib, cabozantinib, ceritinib, crizotinib, dasatinib, entrectinib, erlotinib, gefitinib, ibrutinib, imatinib, lapatinib, lenvatinib, midostaurin, neratinib, nilotinib, nintedanib, osimertinib, pazopanib, ponatinib, ruxolitinib, sunitinib, vandetanib.

II) Inhibitors of other kinases, exemplified by PI3K inhibitor like copanlisib, MEK inhibitors like dabrafenib, trametinib, cobimetinib, vemurafenib, cylin.dependent kinase inihibitors like palbociclib, ribociclib, etc.

III) Anti-receptor antibodies, exemplified by bevacizumab, cetuximab, necitumumab, panitumumab, trastuzumab etc.

IV) Genotoxic agents like busulfan cyclophosphamide, chlormethine, chlorambucile, carmustine, doxorubicin, uramustine, bendamustine, ifosfamide, melphalan, mitoxantrone, lomustine, cisplatin, carboplatin, oxaliplatin, picoplatin, etc.

V) Inhibitors affecting DNA synthesis, DNA structure or topoisomerases exemplified by 5-Fluorouracil, 6-Mercaptopurine, capecitabine, cytarabine, floxuridine, fludarabine, gemcitabine, irinotecan, topotecan, camptothecin, etoposide, hydroxycarbamide, methotrexate, pemetrexed, trabectedin, etc.

VI) Immune checkpoint inhibitors like Pembrolizumab, nivolumab, atezolimumab, avelumab, durvalumab, iplimumab, etc.

VI) Hormonal therapy exemplified by tamoxifen, anastrozole, letrozole, exemestane, goserelin, triptorelin, histrelin, abiraterone, degarelix, leuprolide, flutamide, bicalutamide, nilutamide, enzalutamide, etc.

Additionally, sanglifehrin macrocyclic analogues or sanglifehrin macrocyclic esters may be administered in combination with other therapies including, but not limited to, radiotherapy or surgery.

Of particular interest is tyrosine kinase inhibitors, genotoxic agents, and/or immune checkpoint inhibitors.

In a preferred embodiment, the sanglifehrin macrocyclic analogue is a sanglifehrin macrocyclic ester.

In another preferred embodiment, the sanglifehrin macrocyclic analogue has a structure of formula (I), wherein, $R_1$ represents $OR_3$ and $R_2$ represents F;

In a more preferred embodiment, $R_3$ represents alkyl, alkenyl, cycloalkyl, cycloalkenyl, alkylcycloalkyl, alkylcycloalkenyl, alkenylcycloalkyl, alkenylcycloalkenyl, aryl, heteroaryl, alkylaryl, alkylheteroaryl, alkenylaryl or alkenylheteroaryl.

In a preferred embodiment, $R_3$ represents alkyl or alkenyl. Preferred alkyl or alkenyl is a straight or branched alkyl alkenyl having from 1-10 carbon atoms, notably from 1-6 carbon atoms.

In another preferred embodiment, the sanglifehrin macrocyclic analogue has a structure of formula (I), wherein, $R_1$ represents $NR_3R_4$, $R_2$ represents F;

In another preferred embodiment, $R_3$ and $R_4$ represent an alkyl, or cycloalkyl group, which are optionally substituted by monocylic aryl or monocyclic heteroaryl.

The sanglifehrin macrocyclic analogue may have one of the structures below:

11
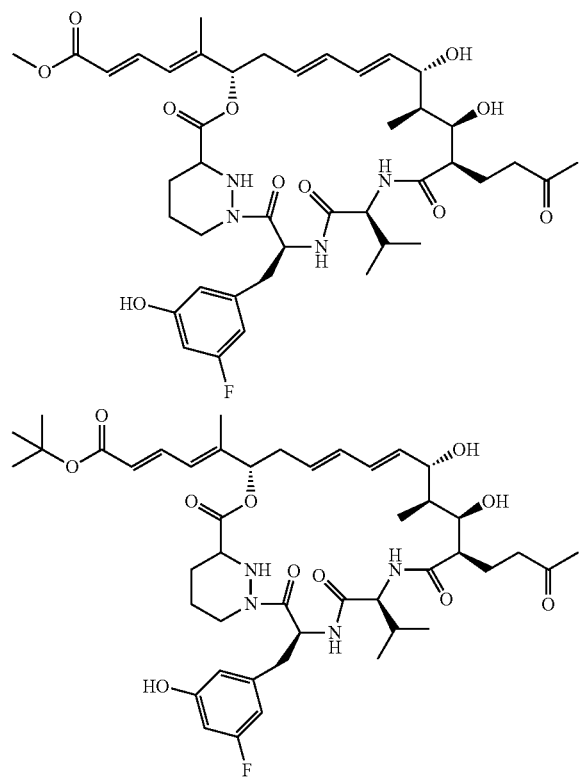
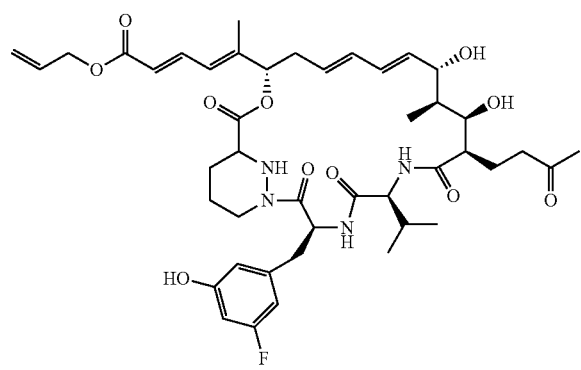
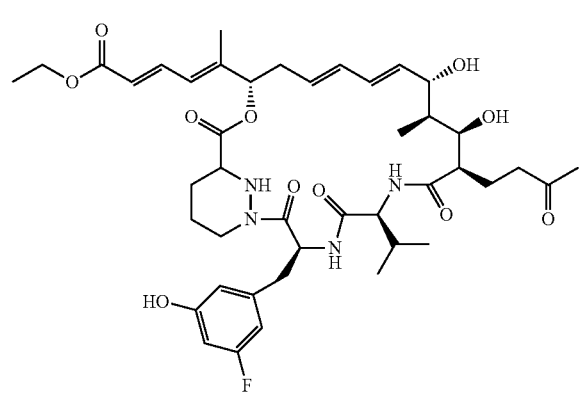
12
-continued
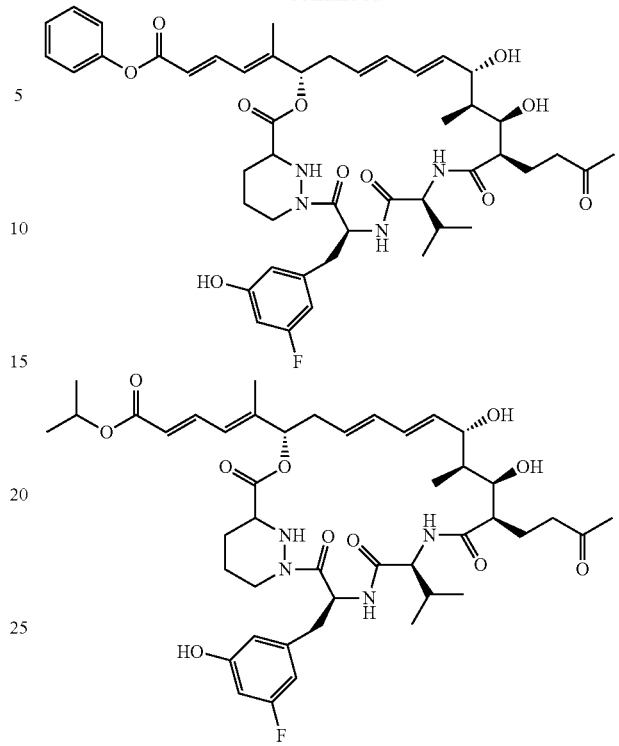
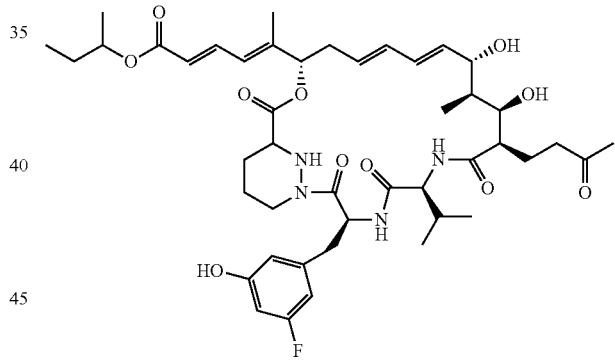
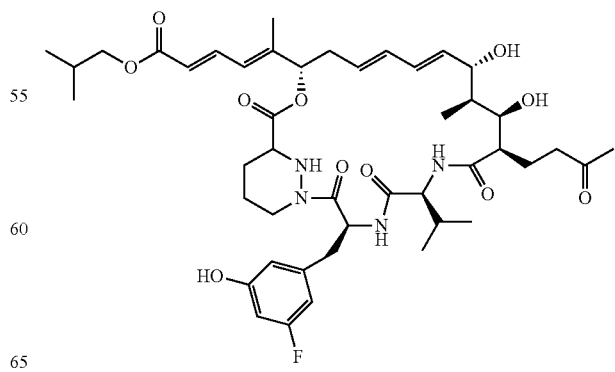

As seen from the examples herein a particular compound of interest is

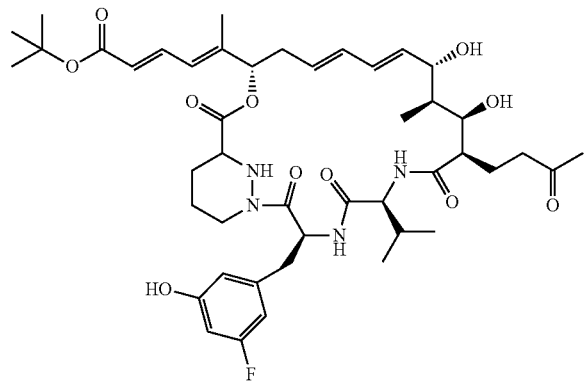 [SMILES: CC(=O)CC[C@H]1C(=O)N[C@@H](C(C)C)C(=O)N[C@@H](Cc2cc(O)cc(F)c2)C(=O)N2CCCC(N2)C(=O)O[C@H](/C(C)=C/C=C/C(=O)OC(C)(C)C)C/C=C/C=C/[C@H](O)[C@H](C)[C@H]1O]

A sanglifehrin macrocyclic analogue may be administered by any conventional and suitable administration route. It may be administered alone or as part of a therapeutic regime with other drug substance. In the present context, co-administration is included to denote any means of delivering two or more therapeutic agents to the patient as part of the same treatment regime, as will be apparent to the skilled person. Whilst the two or more agents may be administered simultaneously in a single formulation this is not essential. The agents may administered in different formulations and at different times.

The formulations may conveniently be presented in a suitable dosage form including a unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

As mentioned herein before, a sanglifehrin macrocyclic analogue may be presented in the form of a pharmaceutical composition, which may contain one or more of the other drug substances mentioned herein or it may be presented in the form of a pharmaceutical kit comprising one or more components, one of which comprising the sanglifehrin macrocyclic analogue and the other(s) comprising another drug substance as mentioned herein. Of particular interest are combination of drug substances as mentioned herein before.

A sanglifehrin analogue will normally be administered by any conventional route for example, but not limited to, orally, parenterally, topically, via a mucosa such as buccal, sublingual, transdermal, vaginal, rectal, nasal or ocular in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses and/or frequencies.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

For example, a sanglifehrin analogue can be administered orally, buccally or sublingually in the form of tablets, capsules, ovules, elixirs, solutions or suspensions, which may contain flavouring or colouring agents, for immediate-, delayed- or controlled-release applications.

Solutions or suspensions of a sanglifehrin analogue suitable for oral administration may also contain one or more solvents including water, alcohol, polyol etc. as well as one or more excipients such as pH-adjusting agent, stabilizing agents, surfactants, solubilizers, dispersing agents, preservatives, flavors etc. Specific examples include excipients e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate).

Such tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxypropylcellulose (HPC), macrogol 8000, sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations in accordance with the present invention suitable for oral administration may be presented as discrete units such as capsules, cachets or tablets, each containing a predetermined amount of the active ingredient; as multiple units eg in the form of a tablet or capsule: as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

Pharmaceutical compositions adapted for topical administration may be formulated as ointments, creams, emulsions, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either suspended or dissolved in the vehicle. In preparing solutions the active ingredient can be dissolved in water for injection and filter sterilised before filling into a suitable vial or ampoule and sealing.

Advantageously, agents such as local anesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

A sanglifehrin analogue may also be administered using medical devices known in the art. For example, in one embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system The dosage to be administered of a compound of the invention will vary according to the particular compound, the disease involved, the subject, and the nature and severity of the disease and the physical condition of the subject, and the selected route of administration. The appropriate dosage can be readily determined by a person skilled in the art.

The compositions may contain from 0.1% by weight, from 5-60%, or from 10-30% by weight, of a compound of invention, depending on the method of administration.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

EXAMPLES

Figure 1:
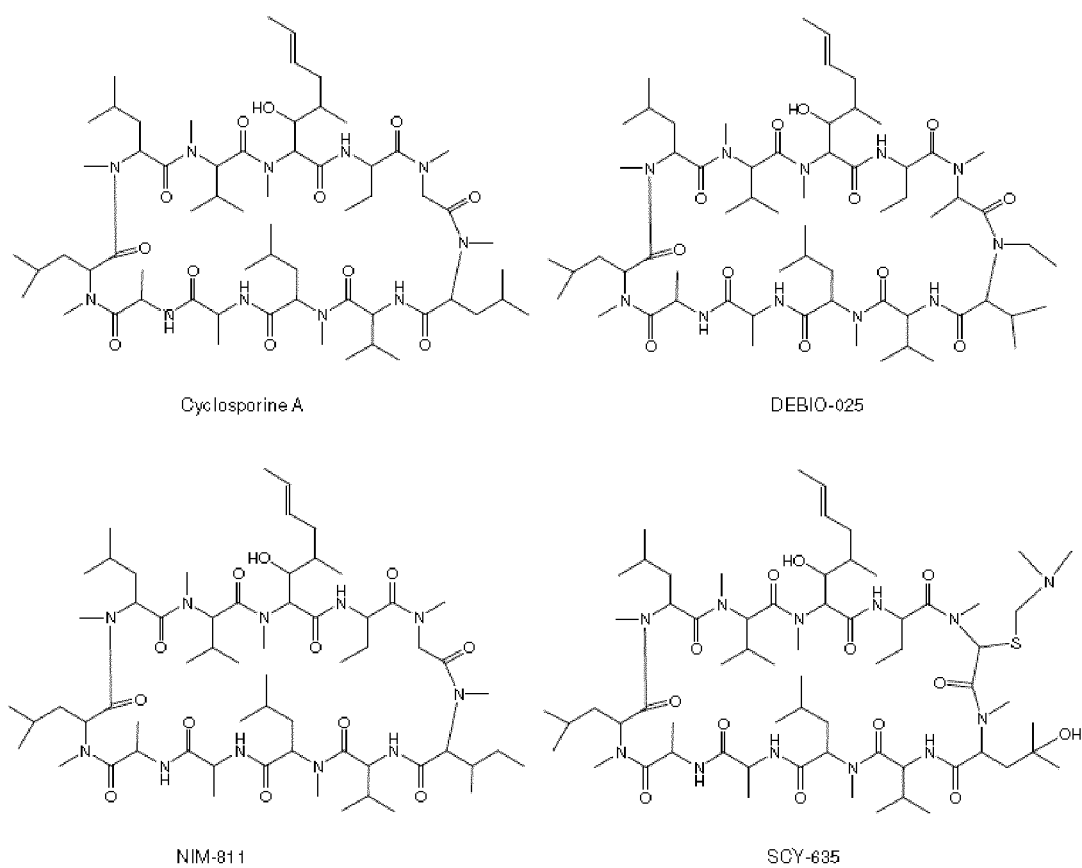
FIG. 1: Structure of cyclosporine A and analogues
Figure 2:
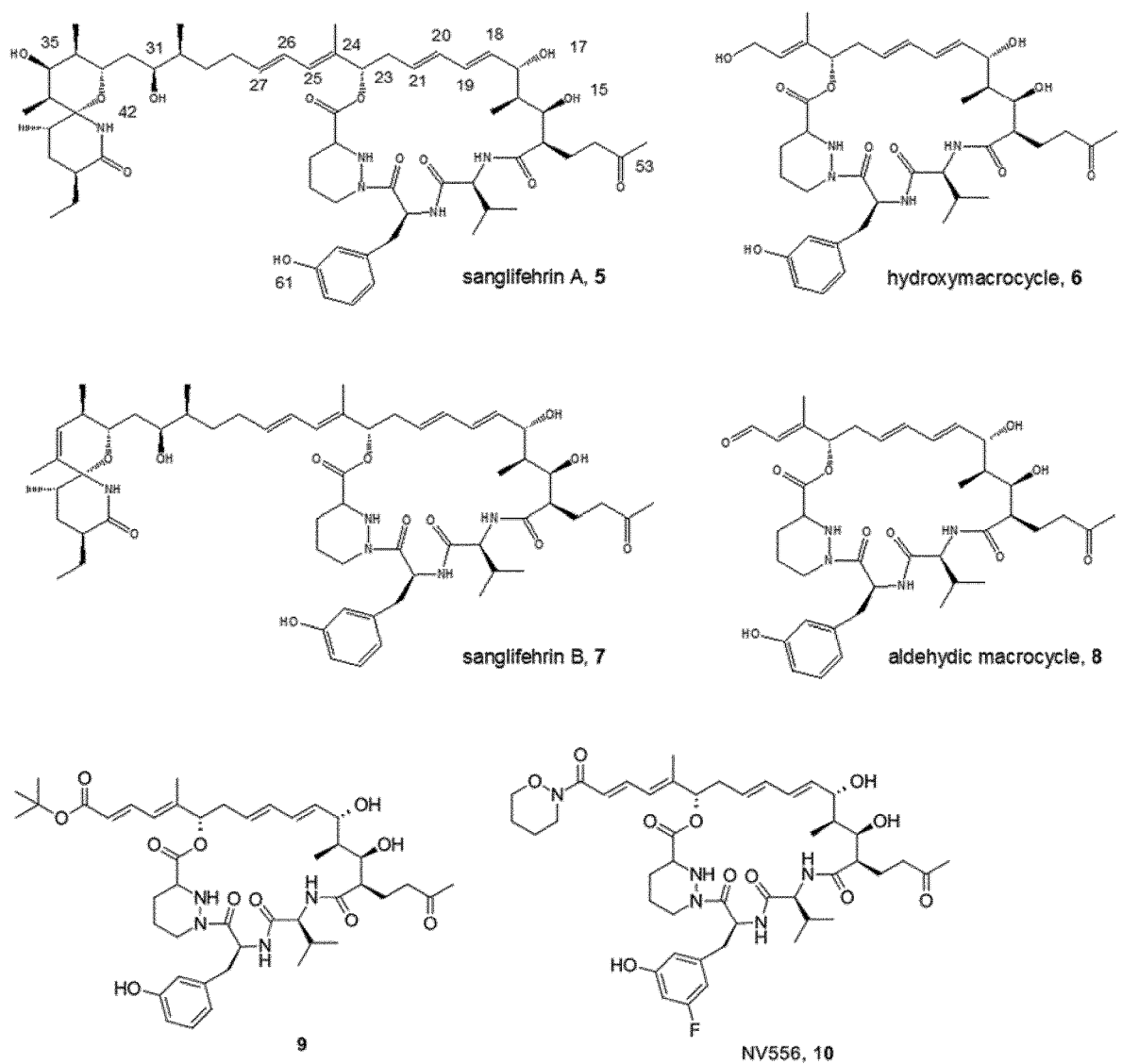
FIG. 2: Structure of sanglifehrin A and analogues

Materials & Methods
Materials

Unless otherwise indicated, all reagents used in the examples below were obtained from commercial sources.
Compound Generation Compounds of the invention are generated using methods as described in WO2011/098809, WO2011/144924, WO2011/098808, WO2012/085553, WO2011/098805, WO2012/131371 and WO2012/131377.
In Vitro Bioassays of Anticancer Activity The cells were seeded in a 96-well plate, test compound or DMSO was added and the plate was incubated for additional four days or 7 days (Calcein AM assay). Viable cell counts were determined after detachment by treatment with trypsin either by trypan blue exclusion, flow cytometry, indirectly by measuring ATP content by addition of an ATP measuring reagent (CellTiter Glo), or Calcein AM, prepared according to the instruction of the manufacturer directly.

Percentage inhibition in the ATP test was calculated by the formula described below:

Growth inhibition %: 100−100×(Experimental−Blank)/(DMSO−Blank)

XLfit software ((Fit model: Dose response one site/$F(x)$ [fit=(A+((B−A)/(1+((C/x)^D))))]) for curve fitting and IC50 calculation) was used for curve fitting and IC50 calculation.
In Vivo Assessment of Anticancer Activity The HUH-7 (Human Liver tumor) cell or another cell line was cultured in DMEM (Low glucose)+2 mM L-glutamine with fetal bovine serum added to a final concentration of 10%. The cell line was sub-cultured by removing and discarding the culture medium. The cell layer was rinsed briefly with 0.25% (w/v) Trypsin-0.53 mM EDTA solution to remove all traces of serum that contains trypsin inhibitor. Thereafter, 2.0 to 3.0 mL of Trypsin-EDTA solution was added to the flask and the cell layer was observed under an inverted microscope until detached. The cells were aspirated by gentle pipetting after addition of 6.0 to 8.0 mL of complete growth medium. A sub-cultivation ratio of 1:1 to 1:2 was used and the culture flasks were incubated at 37° C. with medium renewal two to three times per week.

BALB/c nude female mice, 6-8 weeks, weighing approximately 18-20 g were maintained in a special pathogen-free environment and in individual ventilation cages (4-6 mice per cage). An acclimation period of approximately one week was used between animal receipt and tumor inoculation in order to accustom the animals to the laboratory environment. All cages, bedding, and water were sterilized before use. The mice were inoculated subcutaneously in the right flank with HUH-7 tumor cells ($1\times10^6$ cells/mouse) in 0.2 mL mixture of base media with 50% Matrigel. The treatments were started when the average tumor size reached approximately 150 mm$^3$-180 mm$^3$. Body weight was determined and tumor size measured with a caliper two times per week.

In vitro evaluation of compounds for anticancer activity in a panel of human tumour cell lines in a monolayer proliferation assay were carried out at Shanghai Chempartner. The characteristics of the selected cell lines is summarised in Table 1.

TABLE 1

Test cell lines

| # | Cell line | Origin |
|---|---|---|
| 1 | A-375 | skin, malignant melanoma |
| 2 | U251 | brain, human glioma |
| 3 | HCT 116 | colon, carcinoma |
| 4 | A2780 | ovary, carcinoma |
| 5 | Hep G2 | Liver, carcinoma |
| 6 | Huh-7 | Liver, carcinoma, |
| 7 | SK-Hep-1 | Liver, adenocarcinoma |
| 8 | A549 | lung, carcinoma |
| 9 | PANC-1 | pancreas, ductal carcinoma |
| 10 | RPMI 8226 | myeloma, plasmacytoma, B lymphocyte |
| 11 | PC-3 | prostate, adenocarcinoma |
| 12 | HT-29 | colon, adenocarcinoma |
| 13 | MDA-MB-231 | Breast, carcinoma |
| 14 | Hep3B2.1-7-Luc | Liver, carcinoma |
| 15 | LIXC-003 | Liver, carcinoma |
| 16 | LIXC-004 | Liver, carcinoma |
| 17 | LIXC-006 | Liver, carcinoma |
| 18 | LIXC-011 | Liver, carcinoma |
| 19 | LIXC-012 | Liver, carcinoma |
| 20 | LIXC-066 | Liver, carcinoma |
| 21 | LIXC-086 | Liver, carcinoma |

Example 1. Generation of Compound 1

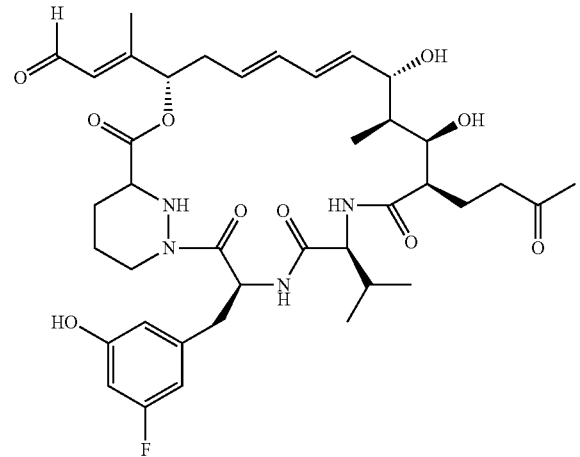

compound 2

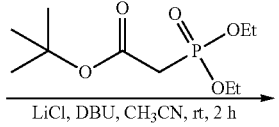

LiCl, DBU, CH$_3$CN, rt, 2 h

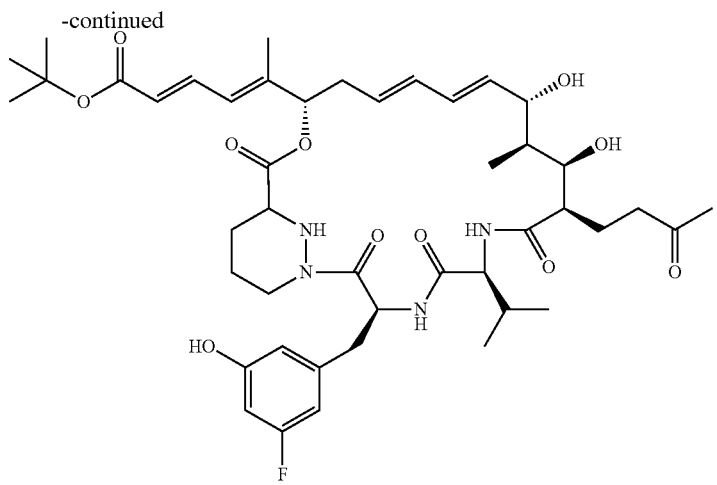

Compound 1

To a mixture of compound 2 (Hansson et al., 2015, Chemistry & Biology 22, 285-292 and WO 2012/131377, 50 mg, 0.066 mmol), tert-butyl diethylphosphonoacetate (50 mg, 0.198 mmol) and LiCl (8.3 mg, 0.198 mmol) in CH$_3$CN (1 mL) was added dropwise a solution of DBU (20 mg, 0.132 mmol) in CH$_3$CN (0.2 mL) at room temperature. The resulting mixture was stirred at room temperature for 2 hours. The reaction mixture was diluted with water and extracted with EtOAc twice. The combined organic layers were washed with brine, dried over Na$_2$SO$_4$, filtered and concentrated under reduced pressure. The residue was purified by column chromatography twice (first time using petroleum ether/EtOAc as eluent and then DCM/MeOH) to afford compound 1 as light yellow solid.

Example 2. In Vitro Bioassay for Anticancer Activity

Figure 3:
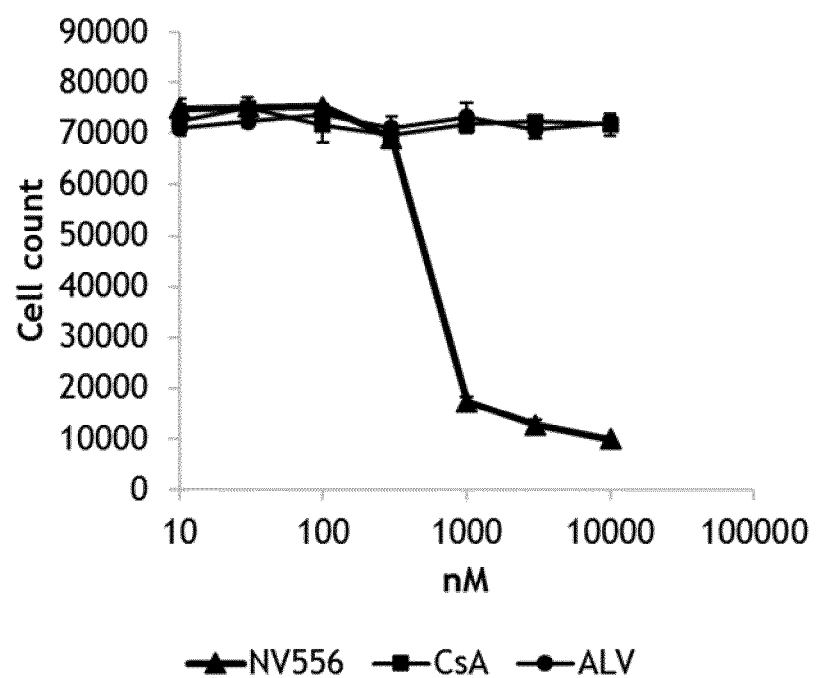
FIG. 3: In vitro evaluation of anticancer activity of sanglifehrin macrocyclic analogue NV556, and cyclosporine based cyclophilin inhibitors cylcosporin A (CsA) and alisporivir (ALV) on the hepatocellular carcinoma cell line HepG2. Viable cell counts were determined from triplicate samples after four days of incubation in the presence of test compounds.

In vitro evaluation of anticancer activity of sanglifehrin macrocyclic analogue NV556, and cyclosporine based cyclophilin inhibitors cyclosporine A (CsA) and alisporivir (ALV) on the hepatocellular carcinoma cell line HepG2. Viable cell counts were determined from triplicate samples after four days of incubation in the presence of test compounds. The results are shown in FIG. 3.

Example 3. In Vitro Bioassays for Anticancer Activity

In vitro evaluation of a sanglifehrin macrocyclic analogue (NV556) for anticancer activity in a panel of 11 human tumour cell lines in a monolayer proliferation assay was carried out as described in the general methods above. Data are means from two independent experiments testing 10 concentrations (3 nM-25 µM) in duplicate.

| Cell line | Maximum inhibition (%) | Concentration giving 50% of maximum effect (µM) |
|---|---|---|
| A375 | 87.6 | 2.1 |
| U251 | 62.0 | 16.9 |
| HCT 116 | 88.7 | 0.1 |
| A2780 | 83.7 | 0.1 |
| HepG2 | 80.6 | 0.1 |
| Huh-7 | 22.4 | 0.03 |
| SK-Hep-1 | 94.6 | 0.1 |
| A549 | 45.2 | 0.1 |
| PANC-1 | 51.0 | 1.3 |
| RPMI 8226 | 87.1 | 0.2 |
| PC-3 | 45.3 | 0.3 |
| HT-29 | 56.8 | 41.6 |
| MDA-MB-231 | 49.9 | 0.5 |

Example 4. In Vitro Bioassays for Anticancer Activity

Figure 4:
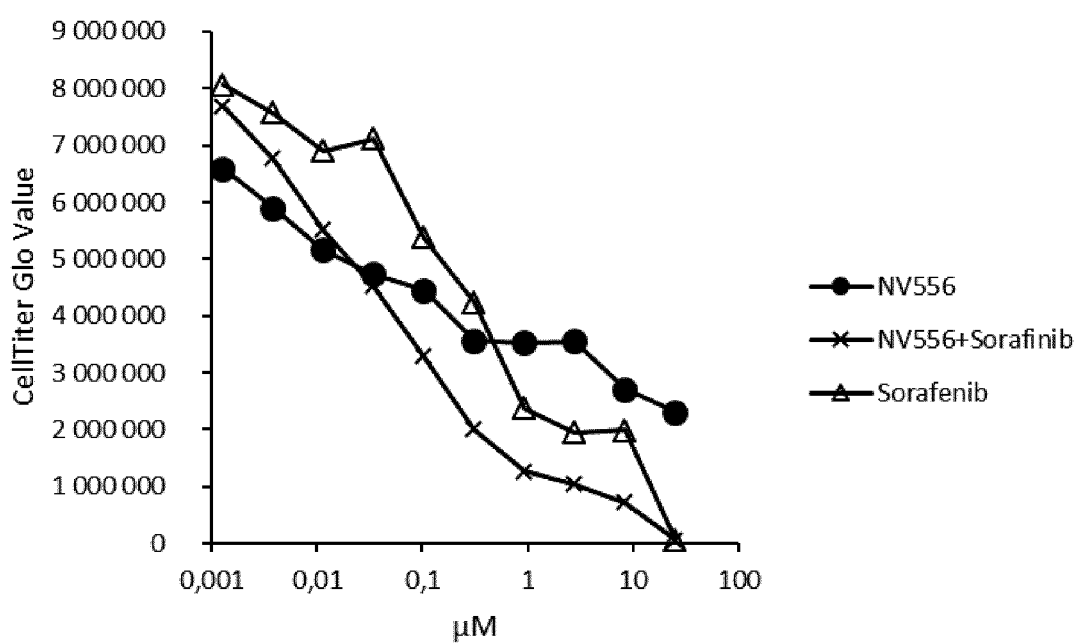
FIG. 4: shows results of in vitro evaluation of combined anticancer activity of a sanglifehrin macrocyclic analogue with the anticancer agent sorafenib against the SK-Hep-1 tumour cell line in a monolayer proliferation assay
Figure 5:
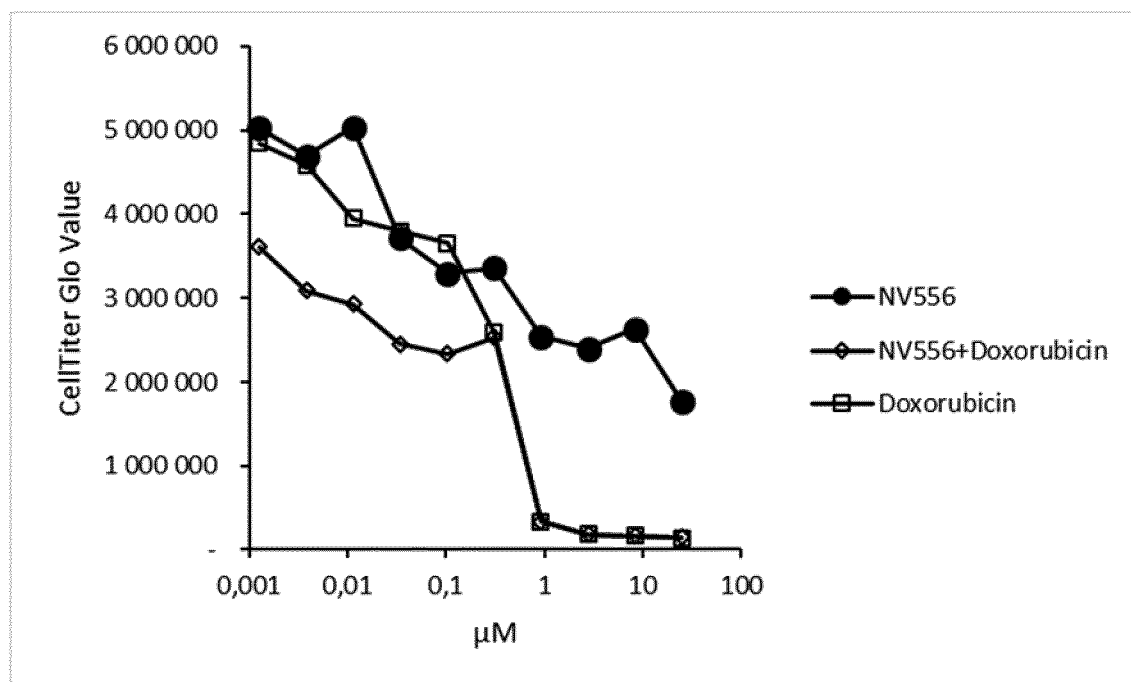
FIG. 5: shows results of in vitro evaluation of combined anticancer activity of a sanglifehrin macrocyclic analogue with the anticancer agent doxorubicin against the SK-Hep-1 tumour cell line in a monolayer proliferation assay

In vitro evaluation of the combined anticancer activity of a sanglifehrin macrocyclic analogue with the anticancer agents sorafenib or doxorubicin against the SK-Hep-1 tumour cell line in a monolayer proliferation assay was carried out as described in the general methods above. The results are shown in FIGS. 4 and 5.

As can be seen from the data, the combination of NV556 and sorafenib or NV556 and doxorubicin displayed a stronger reduction in cell numbers than either compound alone over certain concentration ranges.

Example 5. In Vitro Bioassays for Anticancer Activity

In vitro evaluation of a sanglifehrin macrocyclic analogue (1) for anticancer activity against human hepatocyte cancer cell lines in comparison with NV556 (10) a 7-day proliferation assay. The cell numbers were determined by Calcein AM staining as described in the methods section. Data are from one experiment with each cell line testing duplicate samples of 9 concentrations of each compound. Both compounds were included in each experiment.

| | IC$_{50}$ (nM) | |
|---|---|---|
| Cell line | NV556 (10) | Compound 1 |
| Hep3B2.1-7-Luc | 54 | 11 |
| LIXC-002 | 39 | <3 |

-continued

| Cell line | IC$_{50}$ (nM) | |
|---|---|---|
| | NV556 (10) | Compound 1 |
| LIXC-006 | 62 | 9 |
| LIXC-066 | 244 | 93 |
| LIXC-086 | 9491 | 905 |

As can be seen from the data, compound 1 was more potent (3-10-fold) than NV556 (10) in all cases.

Example 6. In Vitro Bioassays for Anticancer Activity

In vitro evaluation of a sanglifehrin macrocyclic analogue (1) for anticancer activity against human hepatocyte cancer cell lines in comparison with the cyclophilin inhibitor alisporivir and the kinase inhibitor sorafenib in a 7-day proliferation assay. The cell numbers were determined by Calcein AM staining as described in the methods section. Data are from one single experiment or means of two independent experiments testing duplicate samples of 9 concentrations of each compound. All three compounds were included in each experiment.

| Cell line | IC$_{50}$ (nM) | | | n |
|---|---|---|---|---|
| | Compound 1 | Alisporivir | Sorafenib | |
| HepG2 | 7 | 3131 | 2964 | 2 |
| Hep3B2.1-7-Luc | 9 | 2885 | 3899 | 1 |
| LIXC-003 | 8 | 4729 | 4 | 2 |
| LIXC-004 | 4 | 3809 | 2191 | 2 |
| LIXC-006 | 6 | 993 | 3962 | 2 |
| LIXC-011 | 12 | 8710 | 538 | 1 |
| LIXC-012 | 65 | 3221 | 1152 | 2 |
| LIXC-066 | 169 | 1639 | 1654 | 1 |
| LIXC-086 | 686 | 2251 | 1897 | 1 |

As can be seen from the data, compound 1 was more potent (3-1000-fold) than alisporivir in all cases and more potent (3-600-fold) than sorafenib in 8/9 cases.

Example 7. In Vivo Assessment of Anticancer Activity

Figure 6:
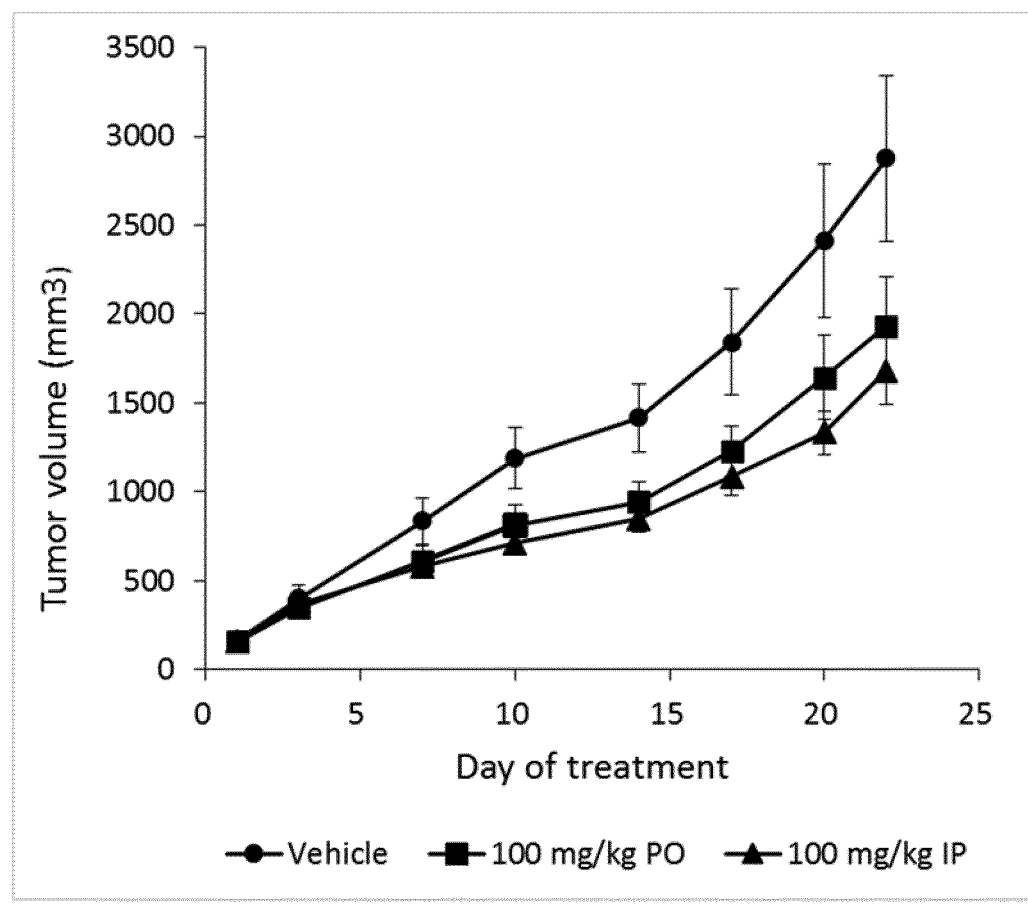
FIG. 6: shows results of in vivo evaluation of anticancer activity of a sanglifehrin macrocyclic analogue against the HuH-7 tumor cell line implanted subcutaneously into mice

NV556 was evaluated for anticancer effect on human HuH-7 hepatocellular carcinoma cell growth in nude mice. The tumor cells were injected subcutaneously in the right flank and treatment with NV556 (10) was initiated when the tumor size had reached 150 mm$^3$-180 mm$^3$. NV556 was administered once daily by oral gavage (PO) or intraperitoneal injections (IP) at a dose of 100 mg/kg (N=8). The results of biweekly tumor measurements (mean and standard error) are shown in FIG. 6.

Example 8. In Vitro Combination of Compound 1 with Sorafenib

Figure 7:
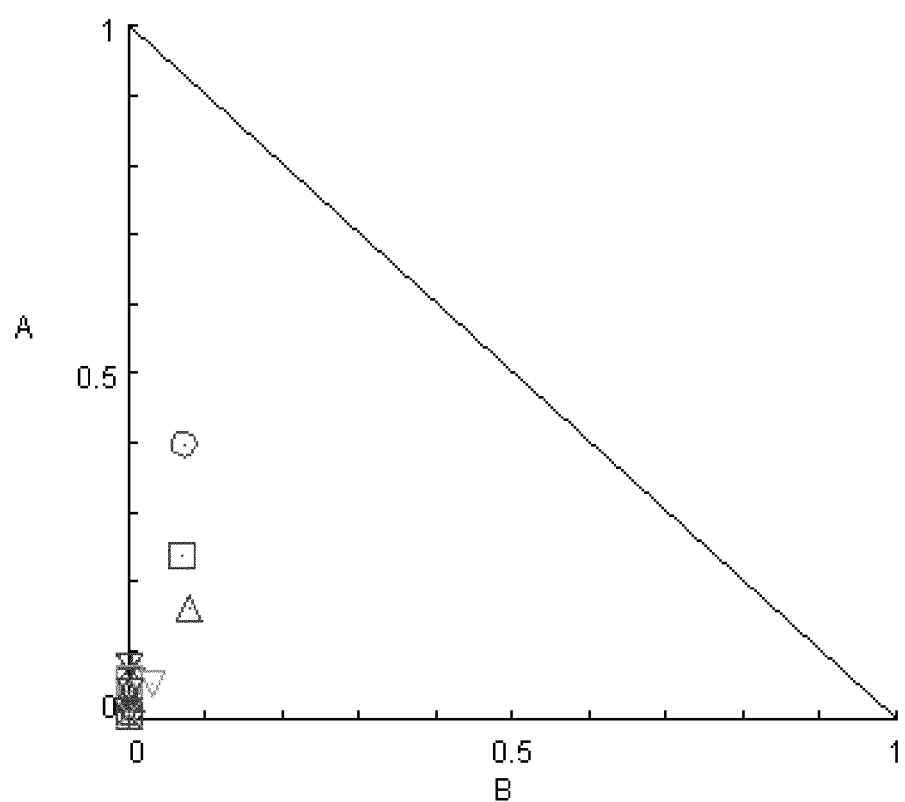
FIG. 7: shows a synergistic growth inhibitory effect by simultaneous treatment of the HepG2 tumor cell line with Compound 1 and the kinase inhibitor sorafenib at different doses in a monolayer proliferation assay

To test for potential synergistic activity with sorafenib, compound 1 (A) was added at a range of concentrations along with a range of concentrations of sorafenib (B) against a liver cancer cell line, HepG2 in a 7-day proliferation assay (Calcein AM assay, described in the methods section). Data are from one single experiment representative of two independent experiments testing duplicate samples. The data was plotted in a normalized isobologram (Chou and Martin. CompuSyn for Drug Combinations: PC Software and User's Guide: A Computer Program for Quantitation of Synergism and Antagonism in Drug Combinations, and the Determination of IC50 and ED50 and LD50 Values, ComboSyn Inc, Paramus, (NJ), 2005) and is shown in FIG. 7. Values at the lower left below the hypotenuse indicate synergism.

The invention claimed is:

1. A sanglifehrin analogue having the structure

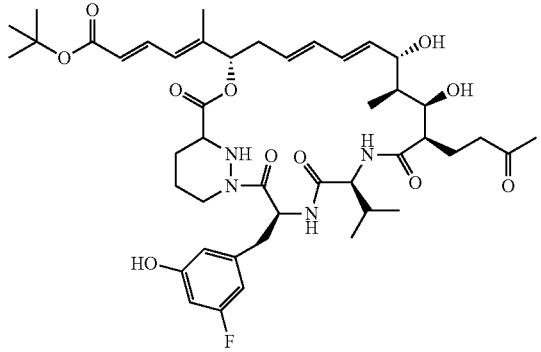 [SMILES: CC(=O)CC[C@H]1C(=O)N[C@@H](C(C)C)C(=O)N[C@@H](Cc2cc(O)cc(F)c2)C(=O)N2CCCC(N2)C(=O)O[C@H](/C(C)=C/C=C/C(=O)OC(C)(C)C)C/C=C/C=C/[C@H](O)[C@H](C)[C@H]1O]

or a pharmaceutically acceptable salt thereof.

2. A pharmaceutical composition comprising a sanglifehrin analogue as defined in claim 1 together with one or more pharmaceutically acceptable excipients.

\* \* \* \* \*